(12) United States Patent
Maloof et al.

(10) Patent No.: US 7,708,723 B2
(45) Date of Patent: May 4, 2010

(54) DEVICE FOR SEALING THE CAPSULAR BAG OF AN EYE AND A METHOD FOR DELIVERING FLUID OR TREATMENT SUBSTANCES TO THE LENS OF AN EYE

(76) Inventors: Anthony Maloof, P.O. Box 155, Kingsford (AU) NSW 2032; Geoffrey Neilson, 7A Hillcrest Avenue, Epping (AU) NSW 2121

(*) Notice: Subject to any disclaimer, the term of this patent is extended or adjusted under 35 U.S.C. 154(b) by 1293 days.

(21) Appl. No.: 10/399,331

(22) PCT Filed: Nov. 28, 2001

(86) PCT No.: PCT/AU01/01554
§ 371 (c)(1),
(2), (4) Date: Aug. 22, 2003

(87) PCT Pub. No.: WO02/43632
PCT Pub. Date: Jun. 6, 2002

(65) Prior Publication Data
US 2004/0010284 A1    Jan. 15, 2004

(51) Int. Cl.
*A61M 35/00* (2006.01)
(52) U.S. Cl. .................. 604/289; 604/294; 606/107
(58) Field of Classification Search ................ 623/6.18, 623/6.21; 606/107; 604/289, 294
See application file for complete search history.

(56) References Cited
U.S. PATENT DOCUMENTS 4,796,623 A * 1/1989 Krasner et al. .............. 606/166

5,540,699 A * 7/1996 Smith ......................... 606/107

FOREIGN PATENT DOCUMENTS

DE     3522998 A1    1/1987
WO    WO 97/47247 A1  12/1997

OTHER PUBLICATIONS

International Search Report; PCT/AU01/01554; published Jun. 6, 2002 as WO 02/43632; entled: A device for seal ing the capsular bag of an eye & a method for delivering fluid or treatment substances to the lens of an eye: Inventors: Anthony Maloof et al.

* cited by examiner

*Primary Examiner*—Kevin C Sirmons
*Assistant Examiner*—Deanna K Hall
(74) *Attorney, Agent, or Firm*—Gottlieb, Rackman & Reisman, PC

(57) ABSTRACT

Disclosed are devices and methods for the transfer of fluids and potentially toxic chemicals into the lens capsule by creating a closed system preventing the fluids from entering the anterior chamber of the eye and thus causing damage to other ocular structures.

The invention comprises one or more fluid conduits which communicate with a plug which maybe inserted through the corneal incision and placed onto the anterior surface of the capsule around the capsulorhexis. The plug is adapted to seal against the anterior surface of the lens capsule.

In preferred embodiments, the flow of fluids into and out of the plug (and therefore the capsule) are controlled from a separate fluid flow controller.

14 Claims, 6 Drawing Sheets

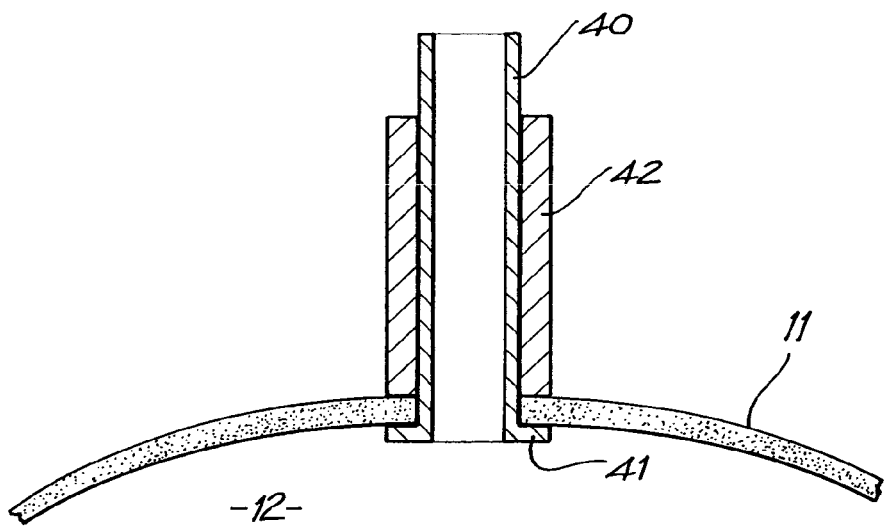
FIG. 3
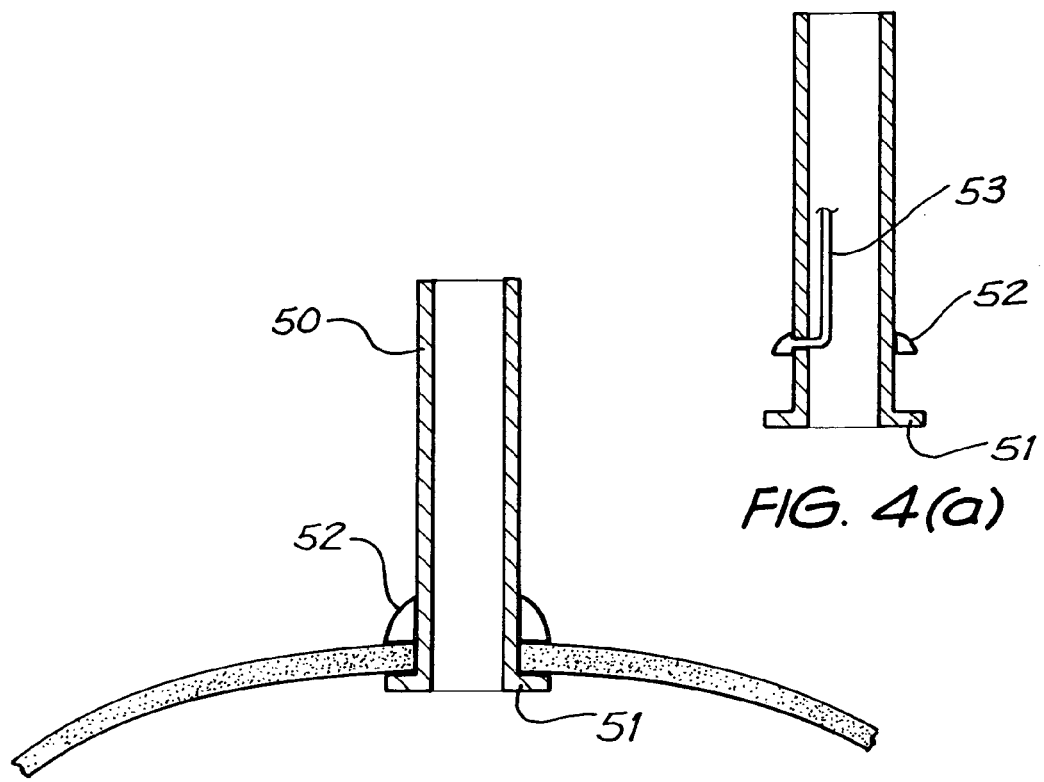
FIG. 4(a)
FIG. 4

DEVICE FOR SEALING THE CAPSULAR BAG OF AN EYE AND A METHOD FOR DELIVERING FLUID OR TREATMENT SUBSTANCES TO THE LENS OF AN EYE

TECHNICAL FIELD

The invention pertains to surgical devices and methods and more particularly to devices and methods for the prevention of posterior capsule opacification following cataract surgery.

BACKGROUND ART

During cataract surgery, the human lens is removed from within the lens capsule and replaced by an artificial lens. This is performed by opening a small hole in the anterior capsule (a capsulorhexis) and then destroying and removing the human lens by phacoemulsification. However, lens cortex and epithelial cells remain following the lens removal, and irrigation/aspiration is routinely used to remove the visible cortex remnants. It is unreasonable to expect all lens epithelial cells (LECs) which are bound to both the anterior and posterior capsule to be removed by this method.

LECs which remain within the capsule have been shown to mutate and grow over the posterior surface of the implanted intra-ocular lens (IOL) thus causing posterior capsule opacification (PCO). This complication of cataract surgery has historically occurred at a rate as high as 30% however recent IOL designs have reduced this to around 2-5% at 2 years. It remains unclear what the longer term rates of PCO with these IOLs will be.

The current treatment for PCO is a Posterior Capsulotomy using a Yag laser. Although the complication associated with this procedure is small, the cost is significant and there is a risk of retinal detachment.

Current methods for reducing the rate of PCO include IOL design. It has been shown that a lens with sharp edges causes a barrier to LEC growth. However, lens capsule fibrosis occurs and these IOLs have been shown to cause vision problems particularly at night due to reflections from these edges.

It has been proposed that cytotoxic chemicals can be used to destroy these epithelial cells, however, there is a risk that these chemicals damage other intranuclear structures.

Research is currently underway into using accommodating IOLs, and clear lens extraction for the correction of refractive errors. However, for these technologies to be successful chronically, the lens capsule must remain flexible and free of fibrosis.

Therefore, there is still a need for a device which overcomes the current problems associated with adequate capsule cleaning and LEC removal.

DISCLOSURE OF THE INVENTION

Accordingly, the invention provides devices and methods for the transfer of fluids and potentially toxic chemicals into the lens capsule by creating a closed system preventing the fluids from entering the anterior chamber of the eye and thus preventing damage to other ocular structures.

The invention comprises one or more fluid conduits which communicate with a plug which maybe inserted through the corneal incision and placed onto the anterior surface of the capsule around the capsulorhexis. The plug is adapted to seal against the anterior surface of the lens capsule.

In preferred embodiments, the flow of fluids into and out of the plug (and therefore the capsule) are controlled from a separate fluid flow controller.

BRIEF DESCRIPTION OF THE DRAWINGS

FIGS. 4 and 4(a) illustrate the use of an inflatable seal between the capsule and the plug.

BEST MODE AND OTHER EMBODIMENTS OF THE INVENTION

Figure 1:
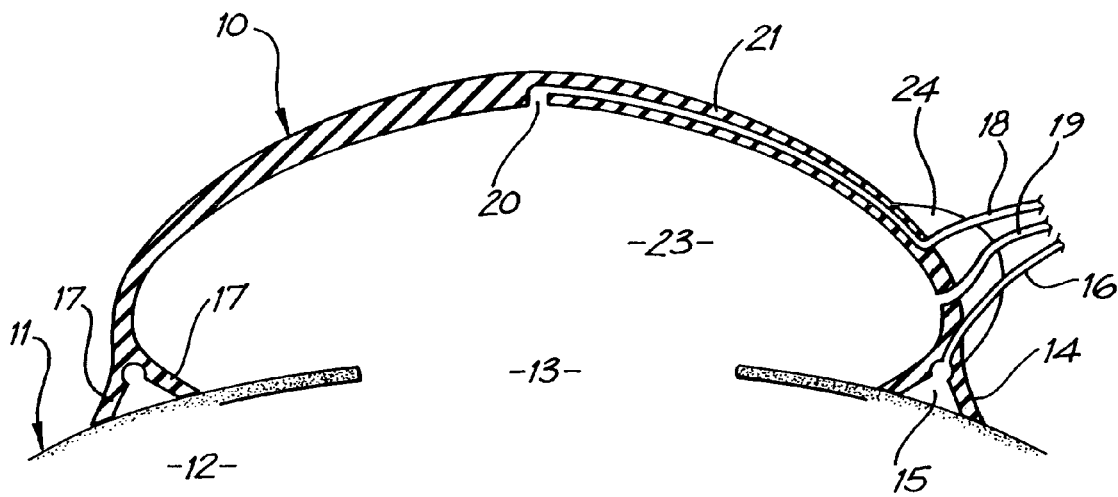
FIGS. 1 and 1(a) are schematic cross sections illustrating the plug and the lumens which carry fluids and vacuum.

As shown in FIG. 1, a first embodiment of the invention comprises a flexible plug 10 which can be inserted through the corneal incision and placed onto the anterior surface 11 of the capsule 12 and around the capsulorhexis 13.

The plug 10 is preferably attached to the anterior surface 11 around the rhexis 13 by a vacuum seal 14. The vacuum seal 14 comprises a circumferential groove 15 which communicates with a lumen 16 which communicates controlled vacuum pressure and extends through the corneal incision. In this example, the vacuum seal is generally circumferential comprising an inverted "v" shaped groove, defined in part by flexible sealing lips 17. Fluid is introduced into and removed from the plug and capsule by the second and third lumens 18, 19. The second lumen 18 is for the aspiration of fluid and leads to an aspiration opening 20 preferably formed at the highest interior point of the plug 10. An aspiration lumen may have a larger internal diameter (ID) than an irrigation lumen.

Figure 1A:
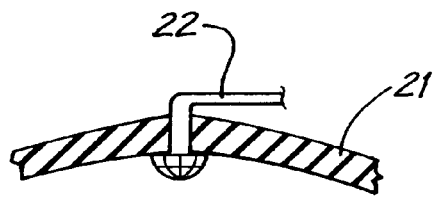

As shown in FIG. 1(a), the aspiration port 20 can be covered by a screen or castellation which prevents the aspiration port from sealing against the capsule and blocking the flow of fluid. A conduit which extends from the lumen 18 to the opening 20 may be embedded within the wall 21 of the plug. In the alternative, the conduit 22 can extend through the wall 21 and to travel outside of the wall 21 as shown in FIG. 1(a).

The third lumen 19 carries the input or irrigation fluid and this lumen 19 also communicates with the interior 23 of the plug 10. It will be understood that irrigation and aspiration may also be achieved through a single lumen, such as the second lumen 18. So long as the irrigation and aspiration steps are performed sequentially, the third lumen 19 maybe omitted.

In some embodiments, the aspiration port 20 and aspiration lumen ID (about 0.3 mm) are larger in diameter than the irrigation inlet and tubing to allow equal flow into and out of the capsule.

In some embodiments, the device is moulded from a material such as silicon or polyurethane such that the device can be rolled into a form allowing it to be passed through the normal cataract corneal incision to the anterior chamber of the eye. An insertion device maybe used for this purpose.

Other forms of the invention feature a stiff handle which is parallel with the infusion/aspiration lumens allowing the device to be positioned onto the capsule. In one form of the invention, the handle is removable. There may also be a web 24 extending tangentially from the edge of the device to meet the tubing and in the same plane as the tubing which is designed to guide the device through the incision on extraction.

Figure 2:
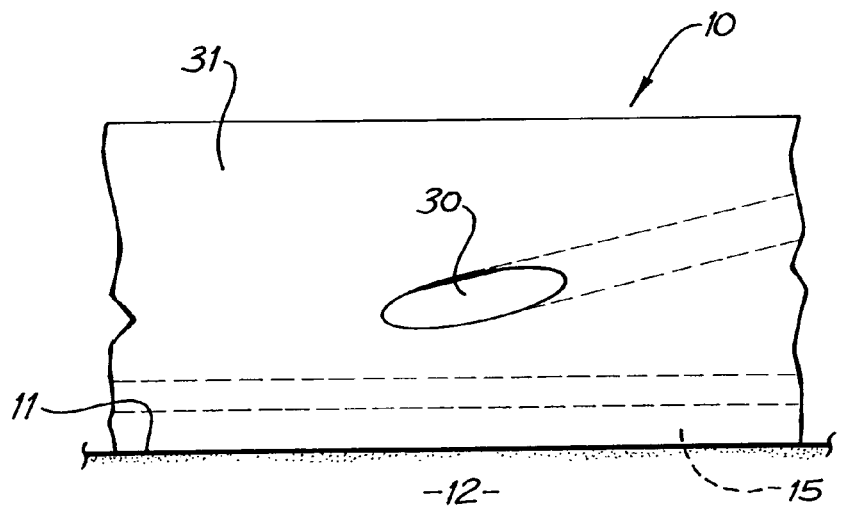
FIG. 2 is a partially sectioned interior view of the plug illustrating an inclined, tangential fluid inlet, FIG. 3 are schematic cross sections illustrating a mechanical engagement between a capsular plug and a capsule.

As shown in FIG. 2, some embodiments of the invention provide an irrigation port 30 which opens through an interior wall 31 of the plug 10. As shown in this FIG. 2, the irrigation port 30 enters the capsule interior 23 both tangentially and inclined toward the interior capsule surface 11. This orientation provides a swirling motion to the irrigation fluid.

As shown in FIG. 3, the plug may take the form of an elongated tube 40. The tube 40 terminates in a flange 41 which passes through the rhexis. A mechanical seal with the capsule is made by lowering a second close fitting tube 42 over the first tube 40 and thereby gripping or clamping the capsule wall 21 between the second tube 42 and the flange 41. This type of plug permits fluids to be introduced and removed directly through the central bore of the tube 40 or through separate lumens which pass through the tube 40.

As shown in FIG. 4, an elongated tube 50 and flange 51 maybe secured and sealed against the capsule by an inflatable seal. As shown in FIG. 4(*a*) the seal 52 comprises an inflatable ring which surrounds the tube 50 above the flange 51. After the flange 51 is inserted through the rhexis and situated against the capsule wall, the seal 52 is inflated, lightly compressing the capsule between the seal 52 and the flange 51. Pneumatic pressure is introduced and withdrawn from the seal 52 by a conduit or lumen 53 which may extend through the inside diameter of the tube 50, for example as shown in FIG. 4(*a*).

In some embodiments, it would be appreciated that with regard to the example shown in FIG. 1, the vacuum pressure control to the vacuum seal 15 is precise. Accordingly, in these cases a controller is provided which has the capability to draw a vacuum, preferably at least 500 mmHg. The vacuum is measured by a pressure or flow sensor such that the infusion of chemicals can be automatically halted if a vacuum leak is detected. Therefore, the controller would accurately measure the vacuum pressure in the seal 15 and immediately halt the flow of irrigation fluid where a pressure drop is detected which could be possibly indicate that chemicals could escape from the sealed capsule.

It will be understood that after the plug is sealed against the capsule, a testing process may be employed which calls for a sequence of the fluids to be passed into the capsule by the controller, first the seal and strength of the capsule is tested using a neutral solution, followed by an active chemical chosen to destroy the LECs, and finally by a solution to flush the active chemical from the capsule. In the alternative, the chemicals in the capsule can be neutralised before the suction is removed and the device is extracted from the interior chamber of the eye.

In preferred embodiments, irrigation and aspiration through the lumens or otherwise, is controlled by pumps such as peristaltic or syringe pumps. The fluid flow controller may be required to prime the infusion and aspiration lines before commencing the procedure. It is important that the fluid flow is controlled such that the fluid volume in the capsule does not exceed the capsule volume.

In an alternate embodiment, the flow of liquid is derived from the pump or plunger position and confirmed by measuring the pressure on the pump roller or plunger, or by measuring the liquid volume in the aspiration vessel.

Two methods of capsule flushing are envisaged. In the first method, the capsule volume is kept constant by ensuring that the irrigation and aspiration flow rates are the same. In the second method, the capsule is first deflated, then inflated by infusing a known volume of fluid or chemical less than or equal to the volume of the capsule. The cycle of inflation and deflation are repeated with a neutral solution to flush the chemical from the capsule.

Figure 5:
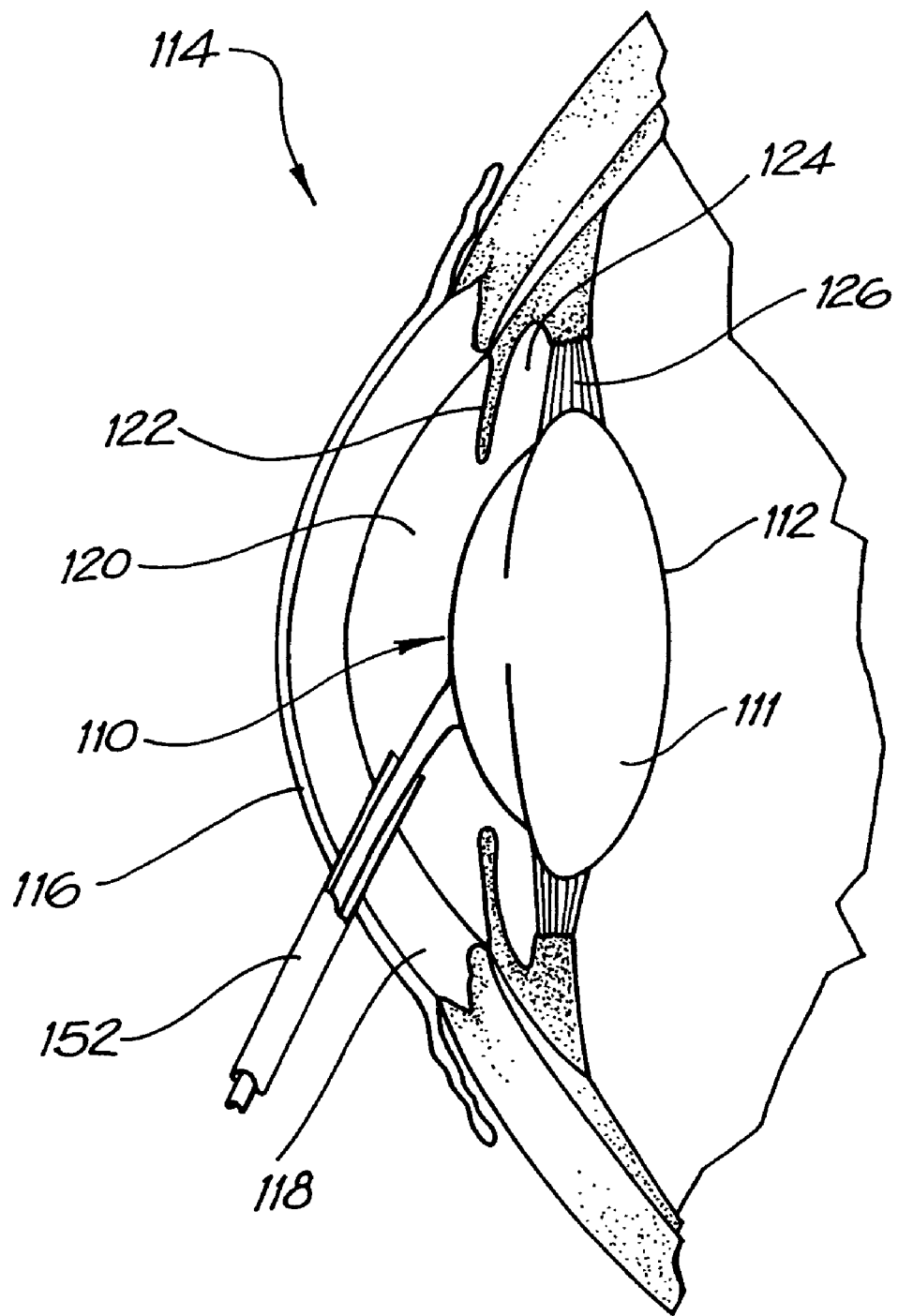
FIG. 5 is a schematic, cross-sectional, side view of an eye showing a first embodiment of a device according to the invention in use.

FIG. 5 shows another embodiment of a device according to the invention, indicated generally by the reference numeral 110, for sealing the capsular bag 111 of the lens 112 of a human eye 114 away from the remaining structures of the eye 114.

The eye 114 is generally composed of a conjunctival 116, a corneal 118, an anterior chamber 20, an iris 122, a posterior chamber 124 and lens zonules 126.

Figure 6:
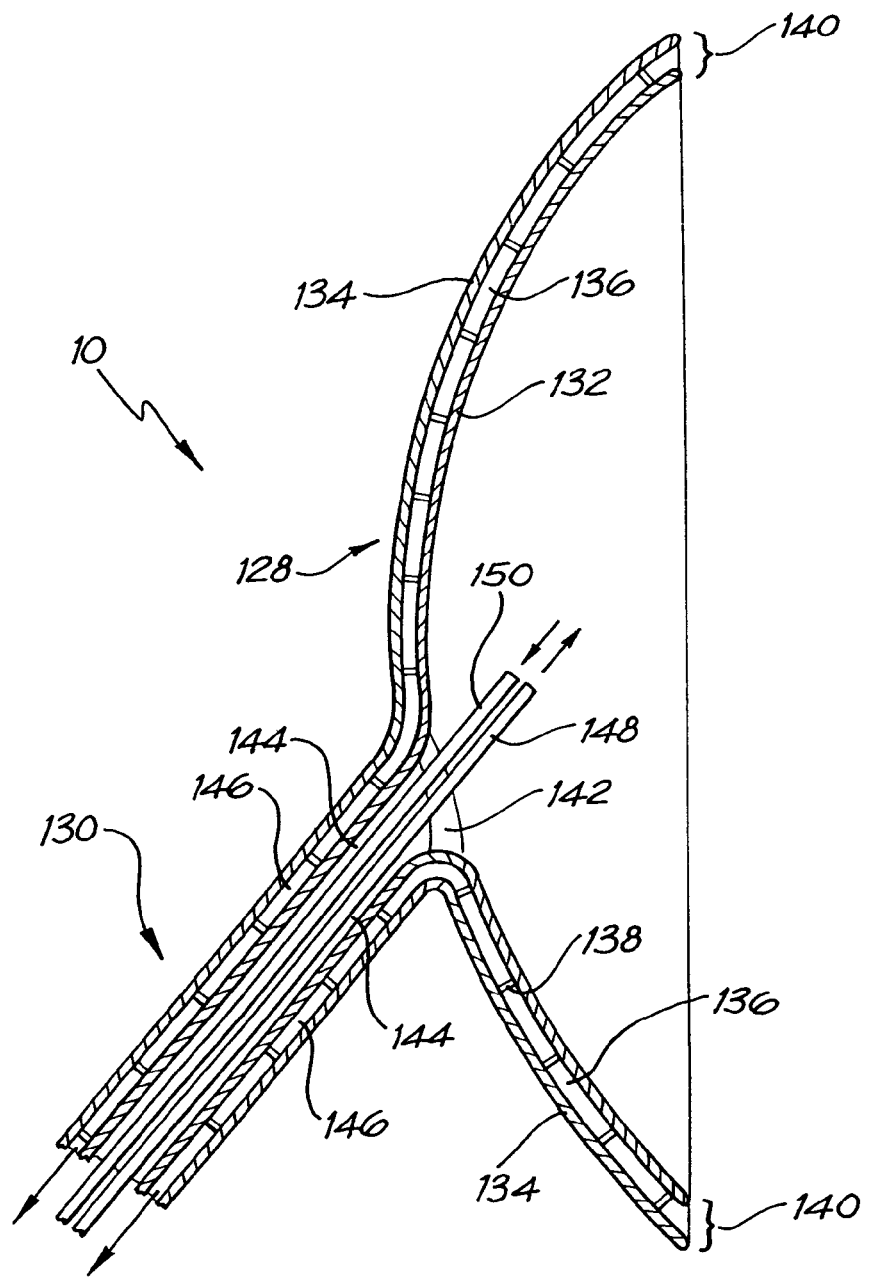
FIG. 6 is a schematic, cross-sectional view of the device shown in FIG. 5.

Referring to FIG. 6, the device 110 includes a cover assembly 128 and a stem 130. The cover assembly 128 has, in use, a substantially spherical-segment, hollow shape and is formed from an inner wall 132 and an outer wall 134 which have a passage 136 therebetween. The walls 132 and 134 are maintained spaced apart to keep the passage 136 open by an array of small spacer columns 138.

The cover assembly 128 is bounded by a peripheral rim 140 which has an annular opening in fluid communication with the passage 136. The rim 140 preferably has an external diameter of 5 to 7 mm. The cover assembly 128 also has an opening 142 in fluid communication with the interior surface of the inner wall 132 and thus with the interior of the cover assembly 128. The stem 130 includes an inner channel 144 that terminates at the opening 142 and an outer annular channel 146 in fluid communication with the passage 136 and thus the annular opening 140. The inner channel 144 preferably has an internal diameter of about 1 mm. The external diameter of the stem 130 is preferably about 3 mm.

Figure 7:
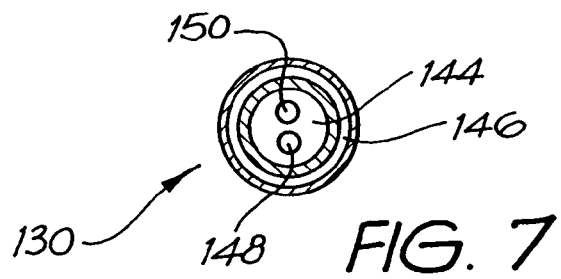
FIG. 7 is a schematic, partial, cross-sectional end view of the device shown in FIG. 6.

Also shown in FIG. 7 are an inspiration tube or lumen 148 and an aspiration tube or lumen 150, which preferably have an internal diameter of about 0.2 to 0.3 mm. The purpose and function of the tubes or lumens 148 and 150 will be described in more detail below.

As shown in FIG. 5, the cover assembly 128 of the device 110 is, in use, positioned by the surgeon against the lens 112 of the eye 114. A preferred method for positioning the cover assembly will now be described with reference to FIGS. 8 to 10.

Figure 8:
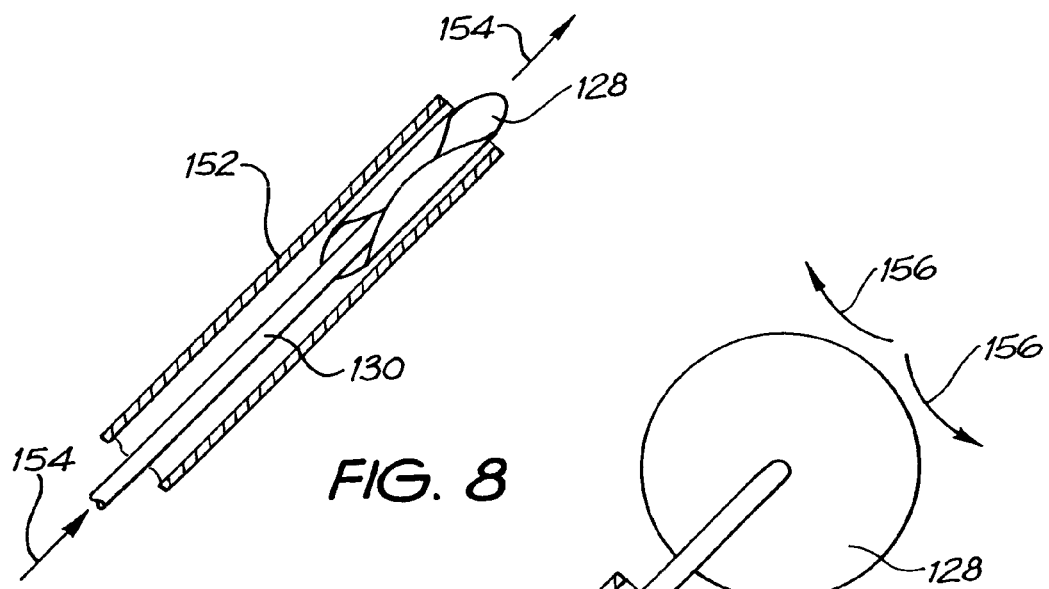
FIG. 8 is a schematic side view of the device within a delivery tube before use.
Figure 9:
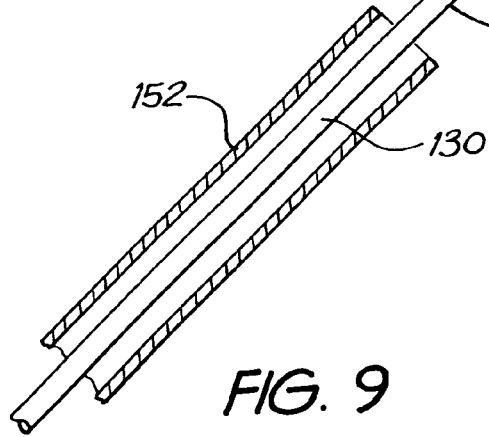
FIG. 9 shows the device and delivery tube shown in FIG. 8 during use.
Figure 10:
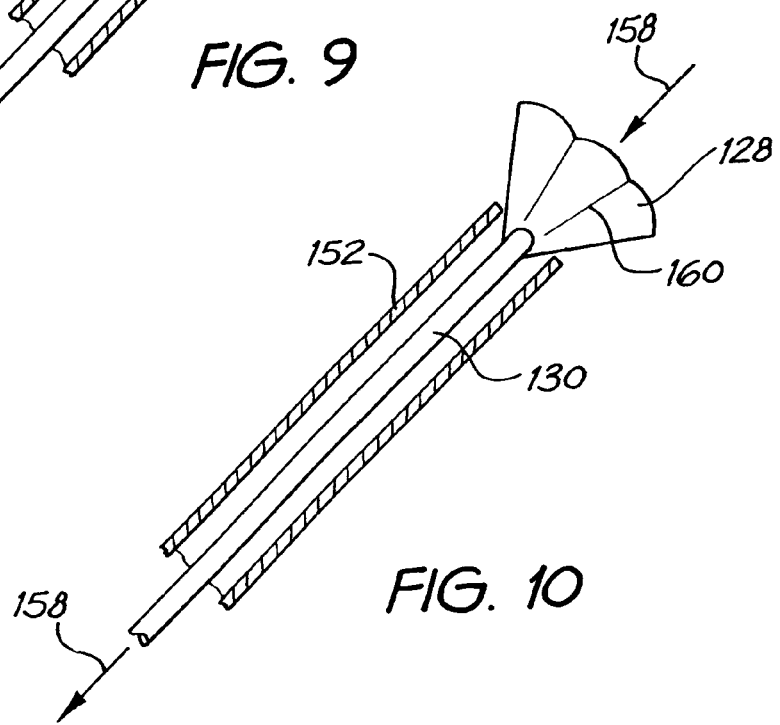
FIG. 10 shows the device and delivery tube shown in FIGS. 8 and 9 after use.

FIG. 8 shows the cover assembly 128 and stem 130 contained within a delivery tube 152. In order to fit within the delivery tube 152, the cover assembly 128 is rolled into a substantially cylindrical configuration. When the device 110 is pushed out an open end of the tube, as indicated by arrows 154, the cover assembly 128 unfurls as a result of its inherent resilience, as indicated by arrows 156, into a substantially spherical segment configuration, as shown in FIG. 9. The device 110 can then be operated in the manner shown in FIG. 5, which will be described in more detail below. After use, the cover assembly 128 collapses whilst being pulled back into the delivery tube 152, as indicated by the arrows 158. The cover assembly 128 may include regions of weakness, such as fold lines 160, to facilitate the collapsing. As the cover assembly 128 is contained within the delivery tube 152 before and after use it is able to be delivered into an anterior and posterior chambers 120 and 124 of the eye 114 by passing the delivery tube 152 through an incision (see FIG. 5) through the coat of the eye 114. It will be appreciated that the use of delivery tubes in positioning surgical instruments in the interior of an eye through a small incision is well known in the art.

The operation of the device 110 whilst in the position shown in FIG. 5 will now be described. The device 110 is positioned with the cover assembly 128 abutting the lens 112. This places the annular opening 140 against the surface of the lens 112. A vacuum of, for example about 200 millimetres Hg, is then applied to the outer channel 146 of the stem 130, for example with a manual, syringe-actuated pump. The vacuum communicates through the passage 136 and results in the annular opening 140 being suctioned to the surface of the lens 112 to form a substantially fluid tight seal therewith. The seal results in a substantially closed cavity being formed between the interior or concave surface of the inner wall 132 of the cover assembly 128 and the lens 112 of the eye 114, thereby sealing the capsular bag 111 away from and the remaining structures of the eye.

The integrity of the seal can be tested by delivering a sterile dyed fluid into the closed cavity through the inspiration tube 148. The dyed fluid is removed via the aspiration tube 150.

Other fluids can then be delivered to the closed cavity through the inspiration tube 148. For example, if the capsular bag 111 of the lens 112 is opened with an incision, fluid can be used to flush out epithelial cells and lens fibres. The closed (sealed) cavity prevents the fluids from reaching other areas of the eye. The inspiration and aspiration tubes 148 and 150 can then be used to flush the cavity and lens clean with saline or other suitable solutions.

The fluids are injected at a lower positive pressure than the vacuum pressure which forms the seal between the annular opening 140 and the surface of the lens 112, so as to not interrupt the seal. This can cause the capsular bag 111 to enlarge. The fluids can be driven through the tubes 148 and 150 with, for example, a manual, syringe actuated, pump or a gravity fed infusion device.

The cover assembly 128 is preferably manufactured from a non toxic, polymeric material, such as silicon, that is sufficiently flexible to be rolled into the substantially cylindrical configuration and sufficiently rigid to maintain the spherical segment shape in the presence of a positive pressure in the cavity.

Figure 11:
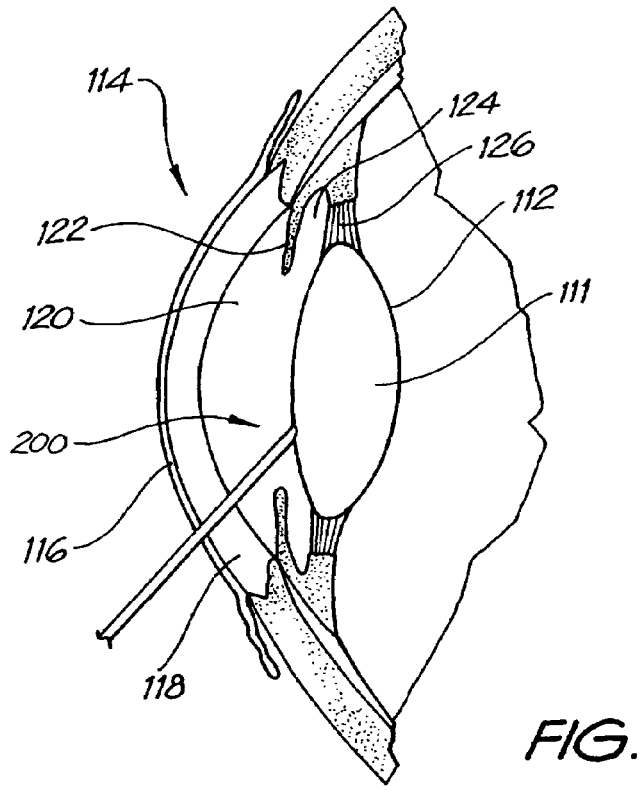
FIG. 11 is a schematic, cross-sectional, side view of an eye showing a second embodiment of a device according to the invention in use.

FIG. 11 shows a second embodiment of a device according to the invention, indicated generally by the reference numeral 200. The reference numerals used in describing the eye 114 in relation to the first embodiment are again used to indicate like features with respect to the second embodiment.

Figure 12:
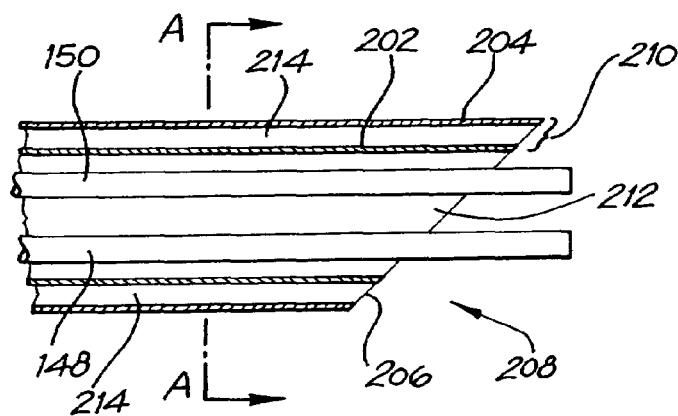
FIG. 12 is a schematic, cross-sectional, side view of the device shown in FIG. 1.
Figure 13:
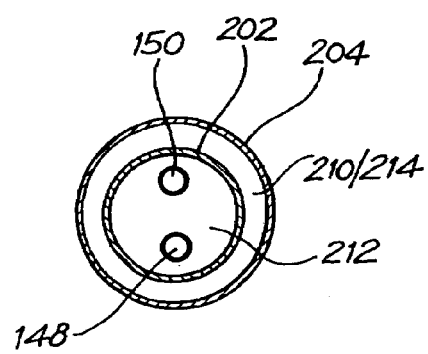
FIG. 13 is a schematic, cross-sectional, end view of the device shown in FIG. 12.

Referring to FIGS. 12 and 13, the device 200 includes inner and outer concentric conduits 202 and 204 respectively. The conduits 202, 204 respectively have an external diameter less then 2 mm and 3 mm and terminate in substantially flush angled ends 206 and 208. The peripheral gap between the ends of the inner and outer conduits 202, 204 defines a rim 210 which functions in a similar manner to the rim 140 of the first embodiment. The distal end of the interior of the inner conduit 202 defines an opening 212 which functions in a similar manner to the opening 142 described in relation to the first embodiment. The gap between the conduits 202, 204 along their length defines a passage 214 which functions in a similar manner to the passage 136 of the first embodiment and is in fluid communication with the rim 210.

The operation of the device 200 is similar to that of the device 110 of the first embodiment and will now be described. The device 200 is positioned by a surgeon as shown in FIG. 1 by passing the distal end of the device 200 through a small (approximately 2.5 mm) incision through the coat of the eye 114. The device 200 is then positioned with its distal end abutting the lens 12. A vacuum is then applied to the passage 214 which results in the opening 210 being suctioned to the surface of the lens 112 to form a substantially fluid tight seal therewith. The seal again results in a substantially closed cavity being formed between the interior of the inner conduit 202 and the lens 112 of the eye 114.

The integrity of the seal can be tested with dye, as was described in relation to the first embodiment. The inspiration and aspiration tubes 148 and 150 (see FIGS. 12 and 13) can then be used as was described in relation to the first embodiment.

The device 210 is preferably manufactured from a non toxic, polymeric material that is sufficiently flexible to be manoeuvrable into the eye and sufficiently rigid to maintain its elongated shape in the presence of negative pressure in the 214 and positive pressure in the interior of the inner conduit 202. The device 200 can be used with a smaller incision in the eye than the first embodiment and a smaller incision (preferably less than 2 mm or most preferably about 1.5 mm) can be used to open the capsular bag 111.

As is evident from the above description, the advantage provided by the invention is that it allows the lens of the eye to be sealed from other areas of the eye. As a result, fluids can be delivered to the lens of the eye, for example to irrigate the capsular bag to remove residual lens fibres and epithelial cells, without allowing those fluids to migrate to other areas of the eye where they could harm cells required for the eye to function correctly.

Although the invention has been described with reference to a specific example, it will be appreciated by those skilled in the art that the invention may be embodied in many other forms.

While the present invention has been disclosed with reference to particular materials and details of construction, these will be appreciated to have been provided by way of example and not as limitations to the scope or spirit of the invention as disclosed.

The invention claimed is:

1. A device for sealing an opening in a capsular bag of an eye and for delivering fluid to and from the capsular bag comprising:

(i) a cover having an inner wall, an outer wall and a plurality of spacers, said inner and outer walls being at least partially spherical and being separated by said spacers to form a spherical first passageway therebetween, the cover having a domed segment defined by said inner and outer walls, said domed segment being sized and shaped to fit over the capsular bag of the eye, said cover further including a circular rim disposed peripherally around said domed segment and in communication with the first passageway, (ii) a stem projecting outwardly from the cover, the stem having an inner annular wall and an outer annular wall with an annular passageway therebetween which is in communication with the first passageway, the inner annular wall defining a central channel that opens into the interior of the cover, said interior of the cover defining a chamber with the capsular bag when said cover is placed over the capsular bag, and (iii) at least one lumen within the central channel of the stem projecting into the interior of the cover for delivering fluids to said chamber and hence the capsular bag, wherein the rim is constructed and arranged to be positioned against the capsular bag and surrounding the opening in the capsular bag wherein a vacuum applied to the first passageway affixes the rim to the capsular bag and seals said chamber when vacuum is applied through said annular passageway, said first passageway and said rim.

2. The device of claim 1 wherein there are two lumens in the central passageway of the stem.

3. The device of claim 2 wherein one of the lumens is an irrigation lumen through which a fluid substance may be delivered to the capsular bag and the other lumen is an aspiration lumen for removing the fluid substance from the capsular bag.

4. The device of claim 1 wherein the device is adapted to be folded or rolled or compressed without damage into a generally cylindrical or semicircular form and is sufficiently flexible and resilient such that it returns to its original shape when released.

5. The device of claim 4 which is adapted to be rolled or folded and inserted into a delivery tube.

6. The device of claim 4 further comprising regions of weakness such as fold lines to facilitate folding or rolling of the device.

7. The device of claim 1 further comprising a controller which provides a specified vacuum through the annular passageway to the rim.

8. The device of claim 3 including an irrigation pump and an aspiration pump which are controlled by a controller such that the fluid volume in the capsular bag does not exceed the capsular volume.

9. The device of claim 8 where an irrigation is halted when a pressure sensor and/or flow meter detects a vacuum leak.

10. A device for performing a surgical procedure on the capsular bag of an eye, said device comprising:
    a cover sized and shaped to fit over the capsular bag, said cover being dome-shaped and having an inner wall and an outer wall, said inner and outer walls being concentric defining a partially spherical space between said inner and outer walls, said cover further including a rim defined peripherally around said cover and forming a peripheral channel along said rim, said channel being in communication with said partially spherical space; and
    a stem having a first end attached to said cover and a second end disposed away from said cover, said stem including a first stem section extending longitudinally through said stem and terminating at said first end in an a first opening disposed bellow said inner wall, said first stem section being separate from and not in fluid communication with said spherical space, said stem further including a second stem section extending longitudinally through said stem and being in communication with said spherical space;
    wherein, when said cover is placed over the capsular bag, a chamber is formed between the inner wall and the capsular bag with said first stem section being in fluid communication with the chamber to provide fluids to the capsular bag, and and said second stem section being used to apply vacuum to said partially spherical space and said channel to seal said cover against the capsular bag.

11. The device of claim 10 further comprising spacers separating said inner and outer walls to maintain said partially spherical space.

12. The device of claim 10 wherein said stem includes a central channel extending longitudinally along said stem, said first stem section including said channel.

13. The device of claim 12 wherein said stem is formed with an annular channel extending longitudinally along said stem and annularly around said central channel, said annular channel forming said second stem section.

14. The device of claim 12 further comprising a second central channel, wherein first central channel provides fluids into said chamber and said capsular bag and wherein fluids from the chamber are withdrawn through said second central channel.

\* \* \* \* \*